United States Patent [19]

Noda

[11] Patent Number: 4,735,843

[45] Date of Patent: Apr. 5, 1988

[54] SELECTIVELY SURFACE-HYDROPHILIC POROUS OR PERFORATED SHEETS

[75] Inventor: Isao Noda, Cincinnati, Ohio

[73] Assignee: The Procter & Gamble Company, Cincinnati, Ohio

[21] Appl. No.: 943,982

[22] Filed: Dec. 18, 1986

[51] Int. Cl.$^4$ .......................... C08F 83/00; B05C 1/16
[52] U.S. Cl. .................... 428/137; 428/474.4; 428/480; 428/500; 428/522; 523/111; 523/201; 525/902
[58] Field of Search ............... 523/201, 111; 525/902; 428/137, 500, 522, 474.4, 480

[56] References Cited

U.S. PATENT DOCUMENTS

| | | | |
|---|---|---|---|
| 3,838,692 | 10/1974 | Levesque | 128/284 |
| 3,929,135 | 12/1975 | Thompson | 128/287 |
| 3,967,623 | 7/1976 | Butterworth et al. | 128/287 |
| 4,062,817 | 12/1977 | Westerman | 523/111 |
| 4,324,246 | 4/1982 | Mullane et al. | 128/287 |
| 4,342,314 | 8/1982 | Radel et al. | 128/287 |
| 4,429,001 | 1/1984 | Kolpin et al. | 428/283 |

FOREIGN PATENT DOCUMENTS 2023069A 12/1979 United Kingdom .
2113731A 8/1983 United Kingdom .

*Primary Examiner*—Joseph L. Schofer
*Assistant Examiner*—Peter D. Mulcahy
*Attorney, Agent, or Firm*—Jerry J. Yetter; Richard C. Witte; Steven J. Goldstein

[57] ABSTRACT

Surface-hydrophilic perforated sheets comprise a fluid-permeable hydrophobic sheet having a multiplicity of holes for fluid passage. The sheets are coated with a rubber-like material insoluble in aqueous fluid but having surface-hydrophilic properties, whereby the surface of the sheet is rendered hydrophilic. The sheets are particularly useful as cover sheets for absorbent structures such as diapers, bandages, and catamenials.

14 Claims, No Drawings

SELECTIVELY SURFACE-HYDROPHILIC POROUS OR PERFORATED SHEETS

TECHNICAL FIELD

This invention relates to fluid-absorbing articles such as bandages, diapers, catamenials, and the like. An improved topsheet for such articles is provided.

BACKGROUND OF THE INVENTION

Absorbent articles such as diapers, bandages, catamenials, and the like, generally comprise an absorbent core which is covered with some type of "topsheet" material which allows passage of body fluids from the skin area being contacted into the absorbent core. The purpose of the topsheet is partly sanitary and partly comfort for the wearer. For example, it is desirable to keep blood or other matter excreted from wounds away from the wound site. Accordingly, bandages typically have a topsheet designed for this purpose. Diaper topsheets are designed to allow urine to flow through and into the core, while giving the impression of skin dryness to the wearer.

Some of the earliest topsheet material was simply gauze; this was followed by various plastic-type materials; in recent years, formed-films of various types have been introduced. The objective with many of these topsheet materials is to allow rapid fluid passage through the topsheet material and into the absorbent core, while preventing re-flow of the fluid from the core back through the topsheet and back onto the skin (i.e., "re-wet").

A number of means have been suggested for improving topsheet material. For example, British Patent Specification No. 2,023,269, Dec. 28, 1979, discloses a disposable diaper comprising an air permeable topsheet to which is applied a surfactant to facilitate fluid passage therethrough. This surfactant is said to be preferably nonionic, and is uniformly impregnated into the topsheet. See also U.S. Pat. No. 3,967,623, issued July 6, 1976, which discloses a disposable absorbent pad having a perforated topsheet, and treated with surfactant to improve fluid flow.

U.S. Pat. No. 3,838,692, issued Oct. 1, 1974, discloses a sheet material suitable for use as a diaper topsheet which is generally hydrophobic in nature but which includes spaced hydrophilic passages to permit liquid to be transmitted through the sheet material. It appears that the preferred way to make this sheet material is by treating a hydrophilic nonwoven material with a hydrophobic composition, such as a rubber latex.

U.S. Pat. No. 3,929,135, issued Dec. 30, 1975, teaches a topsheet material for absorbent structures which is provided with tapered capillary holes to improve the transmission of body fluids to the absorbent core, without re-wet.

It is an object of the present invention to provide topsheet materials having improved fluid passage. It is another object of the invention to provide topsheet materials which have decreased re-wet. It is a further object of the invention to provide top-sheet materials which are prepared from otherwise hydrophobic polymers, but which are selectively rendered hydrophilic by surface modification, thereby improving fluid flow and re-wet performance. It is a further object of this invention to provide improved absorbent articles, such as bandages, diapers, catamenials, and the like, using said topsheet material. These and other objects are secured by the present invention, as will be seen by the following disclosure.

SUMMARY OF THE INVENTION

The present invention provides surface hydrophilic articles comprising a fluid permeable hydrophobic sheet having a multiplicity of holes or channels for fluid passage and having a fluid-directed front face and a back face, said sheet being substantially coated with a rubber-like material insoluble in aqueous fluid but having surface-hydrophilic properties, whereby the surface of said sheet is rendered hydrophilic.

In a highly preferred mode, the article herein has the back face of the sheet coated with said hydrophilic rubber-like material, whereby the front face of said sheet remains hydrophobic and the back face of said sheet is rendered hydrophilic.

The sheets herein can be composed of fibers or, preferably, polymer film, generally, films having a thickness of no greater than 3 millimeters, preferably less than 0.5 mm, most preferably 0.01 to 0.2 mm.

In order to best secure the advantages of this invention, sheets in which the holes each have an average area no greater than 2 square millimeters, preferably from about 0.001 to 1 square millimeters, are used to manufacture absorbent articles. Such sheets are conveniently prepared from thin, flexible polyethylene, polypropylene, polyvinylchloride, polyamide, or polyester film.

This invention also encompasses absorbent articles comprising:

(a) a fluid-retaining core, said core having a fluid-receiving surface;

(b) a fluid-permeable sheet comprising a multiplicity of holes or channels for fluid passage to said core, said sheet having a hydrophobic fluid-directed front face and a back face which adjoins the fluid-receiving surface of said core, said back face being selectively surface-hydrophilic by virtue of a coating of a rubber-like material insoluble in aqueous fluid but having surface-hydrophilic properties.

Such absorbent articles typically use an absorbent core which comprises a fibrous material or a gelling agent for the fluid being absorbed, or mixtures thereof. In general, such absorbent articles have as said fluid-permeable sheet a polymer film having a thickness of from 0.01 mm to 0.2 mm; said film being provided with a multiplicity of holes each having an average diameter (longest dimension) of from 0.1 mm to 1 mm; said holes typically being of a round, ovoid or truncated conical shape. Such articles include infant diapers, adult incontinence garments, catamenials, bandages, incontinence bed pads and the like.

This invention also encompasses a method for enhancing fluid passage through a fluid-permeable sheet while reducing re-wet comprising maintaining the fluid-directed front face of said sheet hydrophobic and coating the back face of said sheet with a rubber-like material insoluble in aqueous fluid but having surface-hydrophilic properties.

All percentages, ratios and proportions herein are by weight, unless otherwise specified.

DETAILED DESCRIPTION OF THE INVENTION

The articles of the present invention comprise a hydrophobic sheet having a multiplicity of holes or channels for fluid passage. Such sheets are well-known in the literature and in commercial practice, especially in the diaper and catamenial arts. Appropriate sheets to be used in the practice of this invention will be disclosed in more detail, hereinafter.

The key element herein is the rubber-like material insoluble in aqueous fluid having hydrophilic properties which is coated onto the hydrophobic sheet to render said sheet selectively surface-hydrophilic. It is to be understood that the coating may be applied to all surfaces of the sheet, or other hydrophobic article, to render the entire surface thereof surface-hydrophilic. However, it is preferred in the manufacture of absorbent articles using said sheets that only the back face of the sheet be rendered surface hydrophilic so that fluid will flow through the hydrophobic front face of said sheet, through the holes and into a fluid-retaining absorbent core material, without so-called "re-wet" by fluids flowing back through the holes in the sheet.

A detailed description of the preparation of the rubber-like surface-hydrophilic material with which the sheets herein are coated follows. In general, the preparation of such material comprises an emulsion polymerization process whereby polymerizable monomers such as styrene, butadiene, divinylbenzene, or the like, or mixtures thereof, are polymerized in the presence of what can be termed a "diblock" co-oligomer ingredient. The diblock co-oligomer ingredient comprises a hydrophobic "tail" group which becomes involved in the polymerization reaction, and a "head" group which has hydrophilic characteristics. For example, the tail group can contain unsaturated bonds, e.g., an oleyl group; and the hydrophilic head can be a group such as polyoxyethylene. During the polymerization reaction the diblock co-oligomer is linked into the rubbery emulsion by its tail group, and the hydrophilic heads become arrayed on the surfaces of the emulsion particles, thereby rendering what would normally be substantially hydrophobic rubber emulsion particles into particles whose surfaces are hydrophilic.

In an alternate mode, the diblock can be "grafted" onto the surface of the preformed emulsion particles.

This emulsion can then be applied onto any desired substrate, to which the emulsion particles adhere and coalesce to provide a coating which is hydrophilic by virtue of the presence of the hydrophilic heads of the diblock ingredient.

It will be appreciated that this method of rendering a surface of a normally hydrophobic polymer selectively surface-hydrophilic is preferred over simply adding surfactant to said polymer. By using the present method, the formulator can apply the coating in a selective manner, e.g., in the present instance, only to one side of the polymer sheet, as may be desired. Moreover, the present method is preferred to methods which simply apply a surfactant-type material to a polymer surface to render it hydrophilic, since surfactants may simply be washed away by fluid coming in contact therewith. In contrast, the rubbery materials herein provide a fluid-stable coating which remains on the surface of the article treated therewith, even in the presence of fluids such as water, urine, blood, and other body fluids. Accordingly, the present invention provides stable sheet materials which can be used as topsheets in diapers, catamenials, incontinent pads, bandages, and the like.

The following illustrates preparation of various rubber-like materials having surface-hydrophilic properties which can be used in the present invention.

PREPARATION AND CHARACTERIZATION OF "SHEL"

(Surface Hydrophilic Elastomeric Latex)

Example I

A surface-hydrophilic elastomer latex based on styrene-butadiene rubber was prepared in the following manner. A mixture of a surfactant solution prepared by dissolving 0.28 g of oleyl ethoxylate having approximately 20 ethoxylate units ("VOLPO-20") in 20 mL of distilled water, an initiator solution prepared by dissolving 0.035 g of potassium persulfate in 20 mL of distilled water, and an additional 16.4 mL of distilled water were placed in a 250 mL thick-walled glass reaction bottle with a magnetic stirring rod. The distilled water used in this reaction was purged with argon for 15 minutes before being used. The reaction bottle containing the solution mixture of surfactant and initiator was purged with argon for 20 minutes and sealed with a rubber gasket which was covered with a metal bottle cap with two holes. The transfer of 1.75 g of styrene into the reaction bottle was made by injecting the monomers through the rubber gasket using a syringe. In a similar manner, the transfer of 5.25 g of 1,3-butadiene was made by condensing it first in a 15 mL graduated cylinder submerged in dry ice and injecting the condensate into the reaction bottle with a syringe. The reaction bottle was then placed in an oil bath set at 60° C. throughout the reaction period with slow agitation of the reaction mixture with a magnetic stirrer for 16 hours to complete the emulsion polymerization.

Approximately 2 mL of the latex product was dried in an oven at 110° C. for at least one hour. From the weight before and after the drying, the solid content of the latex was estimated to be 9.5%. The surface hydrophilicity of the solid product made from the latex was measured in the following manner. A solid film sample of the latex was obtained by placing 1.0 mL of the reaction product onto a 7.5 cm×7.5 cm glass plate and allowing it to dry at room temperature for several days. The surface hydrophilicity of the film was determined by placing 4 μL of distilled water over the film which was kept horizontal and observing the contact angle between the film surface and water sessile drop using a horizontal microscope equipped with a goniometer. The contact angle of water averaged over six measurements was 6.3±0.8°.

EXAMPLE II

A surface-hydrophilic elastomer latex based on styrene-butadiene-acrylic acid copolymer was prepared in the following manner. A mixture of a surfactant solution prepared by dissolving 0.32 g of oleyl ethoxylate having approximately 20 ethoxylate units in 15 mL of distilled water, an initiator solution prepared by dissolving 0.142 g of potassium persulfate in 15 mL of distilled water, and additional 26.4 mL of distilled water were placed in a 250-mL thick-walled glass reaction bottle with a magnetic stirring rod. The distilled water used in this reaction was purged with argon for 15 minutes before being used. The reaction bottle containing the solution mixture of surfactant and initiator was purged with argon for 30 minutes and sealed with a rubber gasket and a metal bottle cap with two holes.

The transfer of 0.07 g of divinylbenzene, 0.526 g of acrylic acid, and 1.75 g of styrene into the reaction bottle was made by injecting through the rubber gasket with a syringe. The transfer of 5.25 g of 1,3-butadiene was made by condensing it first in a 12 mL graduated cylinder submerged in dry ice and injecting the condensate into the reaction bottle with a syringe. The reaction bottle was then placed in an oil bath set at 60° C. throughout the reaction period with slow agitation of the reaction mixture with a magnetic stirrer for 16 hours to complete the emulsion polymerization. Thus a latex having solid content of 7.1% by weight, which was measured by the method described in Example I, was obtained.

The surface hydrophilicity of the solid product made from the latex was measured by the method described in Example I. The average contact angle of a sessile water drop placed on the surface of a film prepared from the latex was 24±2°.

EXAMPLE III

A surface-hydrophilic elastomer latex containing butadiene-ethylene oxide diblock co-oligomer was prepared in the following manner. A 250 mL round bottom flask was flushed witn nitrogen for 30 minutes and then submerged in a dry ice-acetone bath. The transfer of 3.1 g of liquid 1,3-butadiene to the reaction vessel was made after it had been condensed in a 25 mL flask containing calcium hydride and stirred for 3 hours. A solution prepared from 0.033 g of butadiene-ethylene oxide diblock co-oligomer, which had an average molecular weight of 1,845 measured by vapor-phase osmometry and molecular-weight ratio of 2.85 between the ethylene oxide oligomeric segment and butadiene oligomeric segment, dissolved in 15 mL of distilled water, one mL of 1-dodecanemercaptan, an initiator solution prepared by dissolving 0.096 g of potassium persulfate dissolved in 10 mL of distilled water, and additional 5 mL of distilled water were added to the reaction vessel. The water used in this work was freshly distilled just before being used. The flask containing the reaction mixture was sealed, removed from the dry ice-acetone bath, and allowed to warm up until the contents of the flask were melted. The reaction vessel was then heated in an oil bath to about 53° C. and maintained at constant temperature with slow agitation using a magnetic stirrer for 64 hours to complete the emulsion polymerization.

The surface hydrophilicity of the solid product made from the latex was measured by the method described in Example I. The average contact angle of a sessile water drop placed on the surface of a film prepared from the latex was 5.8°.

EXAMPLE IV

A surface-hydrophilic elastomer latex which, even after extensive dialysis, was capable of producing rubbery films having a hydrophilic surface was prepared in the following manner. A 500 mL round bottom flask was flushed with nitrogen gas for 15 minutes and then cooled by submerging in a dry ice-acetone bath. A mixture of 15 g of condensed 1,3-butadiene, 5 g of styrene, 0.4 g of 1-dodecanethiol, a surfactant solution prepared by dissolving 0.8 g of oleyl ethoxylate having approximately 20 ethoxylate units in 40 mL of distilled water, an initiator solution prepared by dissolving 0.4 g of potassium persulfate in 40 mL of distilled water, and an additional 100 mL of distilled water was placed in the reaction vessel. The distilled water used in this reaction was purged with argon for 15 minutes before being used. The flask containing the reaction mixture was sealed, removed from the dry ice-acetone bath, and allowed to warm up until the contents of flask were melted. The reaction vessel was submerged in an oil bath set at 65° C. for 20 hours to complete the emulsion polymerization. A latex having a solid content of 10.5% was obtained.

The surface hydrophilicity of the solid products made from the latex was measured by the method described in Example I. In order to minimize the effect of the possible presence of free surfactant on the surface hydrophilicity of solid product made from the latex, extensive dialysis was applied to the latex by placing about 20 milliliters of latex in a dialysis membrane tube immersed in a large amount of water which was periodically changed. The average contact angles of sessile water drops placed on the surface of solid films prepared from the latex aliquots after various dialysis periods are given in Table I.

TABLE I

| Effect of latex dialysis on surface hydrophilicity. ||
| Dialysis Period (hours) | Contact Angle (degrees) |
| --- | --- |
| 0 | 6.5 |
| 4 | 5.5 |
| 24 | 5.5 |
| 49 | 5.3 |
| 73 | 6.3 |

EXAMPLE V

A latex capable of producing rubbery films which could maintain stable hydrophilic surface for many weeks in air was prepared in the manner similar to that described in Example IV. The surface hydrophilicity of the solid products made from the latex was measured by the method described in Example I. The average contact angles of sessile water drops placed on the surface of solid films which were aged by exposing in air at the room temperature for various periods of time are given in Table II.

TABLE II

| Effect of aging on surface hydrophilicity. ||
| Aging Period (days) | Contact Angle (degrees) |
| --- | --- |
| 2 | 5.7 |
| 4 | 11.3 |
| 7 | 7.5 |
| 9 | 5.8 |
| 17 | 6.0 |
| 62 | 9.0 |

EXAMPLE VI

A surface-hydrophilic elastomer latex capable of producing rubbery films, which could maintain stable hydrophilic surface even after being washed with water for many hours, was prepared in the following manner. A mixture of 2.5 g of 1,3-butadiene, 2.5 g of styrene, 0.0845 g of 1-dodecanethiol, 0.2 g of oleyl ehtoxylate having approximately 20 ethoxylate units, 0.1 g of potassium persulfate, and 45 mL of distilled and argon-purged water was placed in a 250-mL flask, and emulsion polymerization was carried out as described in Example IV. A latex having a solid content of 10.7% was obtained.

The surface hydrophilicity of the solid products made from the latex was measured by the method described in Example I. The average contact angles of sessile water drops placed on the surface of solid films which were washed continuously for different lengths of time in a large amount of distilled water, rinsed under running water, and dried thoroughly are listed in Table III.

TABLE III

| Washing Period (days) | Contact Angle (degrees) |
| --- | --- |
| 0 | 6.1 |
| 20 | 9.3 |
| 40 | 13.5 |
| 60 | 13.2 |

APERTURED SHEETS

Hydrophobic sheet materials of the type typically employed in the practice of this invention can be prepared by methods well-described in the patent literature. For example, according to the process of U.S. Pat. No. 4,324,246 (Mullane and Smith; Apr. 13, 1982) a sample of thermoplastic material such as 0.0038 cm thick polyethylene film is heated above its softening point. (The softening point is the temperature at which the thermoplastic material can be formed or molded and is less than the melting point of the material.) The heated thermoplastic material in sheet form is then brought into contact with a heated forming screen. The forming screen is preferably an apertured wire mesh screen having the desired aperture size, pattern and configuration. A vacuum is used to draw the heated film against the forming screen, thereby forming the film into the desired pattern and having the desired hole sizes. While the vacuum is still being applied to the film, a jet of hot air is passed over the film. The hot air jet perforates the film in a pattern corresponding to the pattern and size of apertures in the forming screen.

Fluid-permeable sheets prepared in the manner of the Mullane, et al., patent are sometimes referred to as "formed films". The caliper of such films is important since, if the caliper is too great, liquid may accumulate in the apertures and not readily pass therethrough. For the manufacture of absorbent articles such as diapers, catamenials, incontinence articles, and the like, the sheets typically have a caliper of less than about 0.075 cm, or preferably less than about 0.064 cm.

Another type of sheet material useful herein is the resilient, 3-dimensional web exhibiting a fiber-like appearance and tactile impression, comprising a fluid-impervious plastic material, with said web having a multiplicity of apertures, the apertures being defined by a multiplicity of intersecting fiber-like elements, all as disclosed in U.S. Pat. No. 3,342,314, Radel and Thompson, Aug. 3, 1982. The Radel and Thompson sheet materials can be prepared using hydrophobic plastics such as polyethylene, PVC, and the like, and are well-known for use in absorbent products such as catamenials, and the like.

Yet another type of sheet material useful herein is described in U.S. Pat. No. 3,929,135 (Thompson; Dec. 30, 1975) and consists of hydrophobic polymer films having holes which are in the form of tapered capillaries. These tapered capillary sheets are also known for use in absorbent articles, including adult incontinence articles. They may be prepared from various hydrophobic polymers, as mentioned hereinabove; typically, low density polyethylene having thickness of from 0.0025 to 0.0051 cm is employed.

In addition to the sophisticated apertured materials mentioned hereinabove, the practice of the present invention may also be undertaken with hydrophobic sheet materials having simple holes punched therethrough.

Moreover, the coatings of the present invention may be applied to any hydrophobic article, not restricted to sheet materials, to render the surfaces of such articles selectively hydrophilic. For example, it may be desirable to coat items such as plastic tubing, laboratory apparatus, medical valves and apparatus (including contact lenses), and the like, in order to make such items wettable by body fluids.

COATING METHOD

One advantage of the rubber-like materials prepared in Examples I through VI herein is that they are in the form of water-based latexes. Such latexes are not thick or gummy, but rather are flowable liquids not unlike typical paint or other flowable coatings quite familiar to the art. For that reason, they are easy to apply.

Application of the latexes herein to the hydrophobic surfaces being treated is routine. For example, application may be achieved by simple dipping, brushing, spraying, or other techniques used in the coating industry. Once the latex is coated onto the sheet, it may be allowed to air-dry or it may be dried by heat, e.g., in a hot air oven or by infrared heat lamps or the coating on the sheet may be passed through heated rollers.

The method of coating the articles herein is not critical to the practice of the invention, but in the case of sheet materials it is generally preferred to use the heated roller method for speed and ease of operation.

A typical coated sheet of the type useful in the manufacture of absorbent structures such as catamenials, diapers, and the like, is described in Example VII. In this Example, the sheet is coated only on its back face in order to achieve what might be termed "uni-directional" fluid flow through the sheet and into an absorbent core.

EXAMPLE VII

A perforated polyethylene film having numerous (approximately 100/cm$^2$) small holes with less than 1 mm diameter is treated with a surface-hydrophilic elastomer latex of the type disclosed herein in Example I having a nonionic head group and capable of forming films having a hydrophilic surface. More specifically, one side of a 4"×4" sample piece of perforated polyethylene (Mullane and Smith, above) is coated with 1 mL surface-hydrophilic elastomer latex diluted with 4 mL of distilled water by spraying. The latex-covered sample is allowed to dry at 23° C. for 24 hours to form a single-side wettable perforated film.

The single-side wettability of the sample is demonstrated in the following manner. The sample is placed on a piece of absorbent material, such as paper towel, with the latex-treated side facing down toward the absorbent. A small droplet of water is placed on the untreated side of the sample. Upon application of a gentle mechanical perturbation, the water droplet quickly disappears from the untreated side by being transferred to the latex-treated side of the sample and eventually to the absorbent material. No observable trace of water is left on the untreated side.

A similar experiment is carried out by using a perforated polyethylene film without any latex treatment. A water droplet placed on top of the surface of the untreated perforated film remains at the initial position without being transferred to the other side facing down on the absorbent nor spread over the top side. Application of mechanical perturbation similar to or greater than that used in the previous experiment does not induce the fluid to transfer across the perforated film.

Another experiment is carried out by using a perforated polyethylene sample similar to the first experiment with one side being treated with a surface-hydrophilic elastomer latex. This time, however, the latex-treated side of the perforated film is facing up and the untreated side is facing down toward an absorbent. A water droplet placed on the sample immediately spreads over the top surface treated with the latex. The transfer of the water to the other side across the perforation is not observed. The surface of the perforated film facing the absorbent material remains dry, while the top side is wet.

A latex prepared by surface grafting rather than copolymerization is as follows.

EXAMPLE VIII

The preparation of a surface-hydrophilic elastomer latex by attaching an amphiphilic diblock co-oligomer surfactant onto the surface of preformed styrene-butadiene rubber latex was carried out in the following manner.

A styrene-butadiene rubber latex was prepared first. A comonomer mixture consisting of 15 g of condensed 1,3-butadiene and 5 g of styrene was dispersed and polymerized in 180 mL of distilled water with 2.8 g of sodium lauryl sulfate emulsifier, 0.4 g of potassium persulfate initiator, and 0.4 g of 1-dodecanol chain transfer agent. A latex having a solid content of 11.0% was obtained. The surface hydrophilicity of the solid film made from the latex was measured by the method described in Example I. The average contact angle of a sessile water drop placed on the surface of a film prepared from the latex was 77.5±4.0°.

The preformed styrene-butadiene latex described above, which produced hydrophobic films, was converted to a surface-hydrophilic elastomer latex by the following procedure. A mixture of 0.22 g of oleyl ethoxylate having approximately 20 ethoxylate units and 0.044 g of potassium persulfate in 3.6 g of ethanol was added to 20 g of the preformed latex. The reaction bottle containing the mixture was purged with argon for 10 minutes and then sealed with a bottle cap and a rubber septum. The reaction mixture was then placed in an oil bath set at 75° C. with slow agitation for 24 hours to complete the modification reaction of latex.

The surface hydrophilicity of the solid film made from the modified latex was measured by the method described in Example I. The average contact angle of a sessile water drop placed on the surface of a film prepared from the modified latex was 5.3°. The stability of the surface hydrophilicity against water was tested by washing the film prepared from the modified latex with an excess amount of water for 20 hours and subsequent drying. The average sessile contact angle of water droplet placed on the extensively washed film was 6.2°.

EXAMPLE IX

An absorbent structure useful as a diaper, catamenial, bandage, adult incontinence pad, or the like, is prepared as follows.

A liquid impervious, flexible backsheet (0.03 mm polyethylene) sheet is laid in a flat position. An absorbent core in the form of a pad comprising air-laid cellulose fibers (optionally containing fluid absorbent hydrogel) is situated on the backsheet.

A "one-way" topsheet according to Example VII is placed over the core, with the hydrophilic side adjacent to said core, and the assembly is bonded together, for example, by gluing.

In use, the hydrophobic side of the topsheet is placed substantially in contact with the user's body, in well-known fashion.

The article of Example IX is also useful as a bed pad, especially for incontinent, bedridden hospital patients.

What is claimed is:

1. A selectively surface-hydrophilic article comprising a fluid permeable hydrophobic sheet having a multiplicity of holes or channels for fluid passage and having a fluid-directed front face and a back-face, said back-face of said sheet being substantially coated with a rubber-like material insoluble in aqueous fluid but having surface-hydrophilic properties, whereby the back-face of said sheet is rendered hydrophilic and the front face of said sheet remains hydrophobic.

2. A sheet according to claim 1 which comprises a hydrophobic polymer film.

3. A sheet according to claim 2 which has a thickness of no greater than 3 millimeters.

4. A sheet according to claim 3 in which the holes each have an average area no greater than 2 square millimeters.

5. A sheet according to claim 5 wherein the average area of the holes is from about 0.001 to 1 square millimeters.

6. A sheet according to claim 5 which is a polyethylene, polypropylene, polyvinylchloride, polyamide or polyester film.

7. An absorbent article comprising:
   a. a fluid-retaining core, said core having a fluid-receiving surface;
   b. a fluid-permeable sheet comprising a multiplicity of holes or channels for fluid passage to said core, said sheet having a hydrophobic fluid-directed front face and a back face which adjoins the fluid-receiving surface of said core, said back face being surface-hydrophilic by virtue of a coating of a rubber-like material insoluble in aqueous fluid but having surface-hydrophilic properties.

8. An absorbent article according to claim 7 wherein the absorbent core comprises a fibrous material, a gelling agent for the fluid being absorbed, or mixtures thereof.

9. An absorbent article according to claim 8 wherein said fluid-permeable sheet comprises a polymer film having a thickness of from 0.01 mm to 0.2 mm, said film being provided with a multiplicity of holes having an average diameter of from 0.1 mm to 1 mm.

10. An absorbent article according to claim 9 wherein said holes are of a round, ovoid or truncated conical shape.

11. A diaper or incontinence garment according to claim 8.

12. A catamenial according to claim 8.

13. A bandage or incontinence pad according to claim 8.

14. A method for enhancing fluid passage through a fluid-permeable sheet while reducing re-wet, comprising maintaining the fluid-directed front face of said sheet hydrophobic and coating the back face of said sheet with a rubber-like material insoluble in aqueous fluid but having surface-hydrophilic properties.

* * * * *